United States Patent [19]

Chasman et al.

[11] 4,192,678

[45] Mar. 11, 1980

[54] N-ALKYL- OR N-ARYL-BENZISOXAZOLONE SCAVENGER COMPOUNDS

[75] Inventors: Richard A. Chasman, Hilton; Wayne F. Erickson, Webster, both of N.Y.

[73] Assignee: Eastman Kodak Company, Rochester, N.Y.

[21] Appl. No.: 960,888

[22] Filed: Nov. 15, 1978

[51] Int. Cl.$^2$ .................. G03C 1/40; G03C 5/54; G03C 7/00; G03C 1/06
[52] U.S. Cl. .................................... 430/214; 430/236; 430/242; 430/272; 430/390; 430/551; 430/559
[58] Field of Search ............... 96/29 D, 56, 77, 74, 96/73, 95, 100 R, 3

[56] References Cited

U.S. PATENT DOCUMENTS

| | | | |
|---|---|---|---|
| 2,286,662 | 6/1942 | Weyde et al. | 96/56 |
| 2,336,327 | 12/1973 | Weissberger et al. | 96/56 |
| 2,846,307 | 8/1958 | Woolley | 96/56 |
| 3,459,548 | 8/1969 | Bloom | 96/3 |
| 3,482,971 | 12/1969 | Bloom et al. | 96/3 |
| 3,582,333 | 6/1971 | Yost et al. | 96/56 |
| 3,980,479 | 9/1976 | Fields et al. | 96/77 |

FOREIGN PATENT DOCUMENTS 2402900  8/1974  Fed. Rep. of Germany .............. 96/77

OTHER PUBLICATIONS

"Color-forming couplers...", Salminen et al., *Research Disclosure* #12711 11/1974 pp. 14–15.

*Primary Examiner*—Richard L. Schilling
*Attorney, Agent, or Firm*—Harold E. Cole

[57] ABSTRACT

Photographic elements, film units and processes are described wherein N-alkyl- or N-aryl-benzisoxazolones are used to scavenge oxidized electron transfer agents in negative-working, color image transfer elements. The scavenger precursor compounds can be located in an emulsion layer or in a dye image-providing material layer, and in a ballasted form can be located in an interlayer.

42 Claims, No Drawings

N-ALKYL- OR N-ARYL-BENZISOXAZOLONE SCAVENGER COMPOUNDS

This invention relates to photography, and more particularly to photographic assemblages for color diffusion transfer photography wherein N-alkyl- or N-aryl-benzisoxazolones are used to scavenge oxidized electron transfer agents.

U.S. Pat. No. 4,076,529 of Fleckenstein et al, issued Feb. 28, 1978, describes various color image transfer elements which employ nondiffusible, redox-dye-releasing compounds which are alkali-cleavable upon oxidation to release a diffusible color-providing moiety. An electron transfer agent (ETA) is oxidized as a function of development. The $ETA_{ox}$ then cross-oxidizes the dye-releasing compound. Interlayers containing scavenging compounds, such as 2,5-di-sec-dodecylhydroquinone, are usually employed in these elements to prevent the ETA which is oxidized as a function of development of one emulsion layer from migrating to adjacent imaging layers where it would cause the "wrong" dye to be released. In the absence of an interlayer scavenger, severe color contamination would result in the final color image. Most scavenger compounds function by becoming oxidized by the oxidized ETA to regenerate the ETA. While certain compounds have been found to be useful for this purpose, compounds which are more effective and which exhibit little or no loss in scavenging efficiency upon long-term keeping are desired.

U.S. patent application Ser. No. 968,890 of Erickson and Ross, entitled "Scavenger Compounds", filed Nov. 15, 1978, describes various ballasted sulfonamidophenols as oxidized ETA scavengers. The specific compounds described herein are not described in this application, however.

Certain benzisoxazolones used as couplers in diffusion transfer elements are described in *Research Disclosure* 12711, November, 1974. These compounds have an imagewise detachable ballast or dye in their coupling position. U.S. Pat. No. 2,846,307 also describes benzisoxazolone couplers which react with oxidized color developing agent to produce an image dye. Neither the particular benzisoxazolones employed in the instant invention nor their use as scavengers for oxidized ETA are disclosed in these two references, however.

U.S. patent application Ser. No. 719,643 of Hinshaw et al, filed Sept. 1, 1976, relates to nondiffusible benzisoxazolones capable of imagewise-releasing a photographically useful moiety such as a color-providing substance in inverse proportion to silver halide development. However, the particular benzisoxazolones employed in the instant invention as scavenger precursors for oxidized ETA in a employing negative-working compounds, color image transfer system are not disclosed.

U.S. Pat. No. 4,139,379 of Chasman et al, issued Feb. 13, 1979, relates to a color image transfer process which employs certain positive-working benzisoxazolones, some of which are similar to those employed herein, as hydrolyzable electron donor precursors in combination with ballasted electron-accepting nucleophilic displacement compounds as the color-providing substances. However, the use of the hydrolyzable electron donors as scavenger precursors in a color image transfer process employing negative-working compounds is not disclosed in the Chasman et al application.

A photographic element in accordance with our invention comprises a support having thereon at least one photosensitive silver halide emulsion layer having associated therewith a negative-working dye image-providing material, and wherein the element contains an N-alkyl- or N-aryl-benzisoxazolone compound. In a preferred embodiment of the invention, the compound has the following formula:

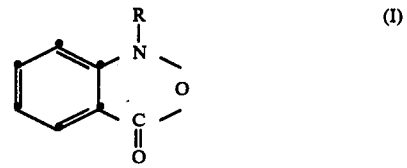

wherein R represents a substituted or unsubstituted alkyl or aryl group. The alkyl group preferably has from 1 to 20 carbon atoms, while the aryl group preferably has from 6 to 10 carbon atoms. For example, R may be methyl, ethyl, propyl, phenyl, benzyl, naphthyl, o-tolyl, p-chlorophenyl, 2-hydroxyethyl, p-anisyl, methoxymethyl, isopropyl, cyclohexyl, etc, so long as R is not a group which is cleavable under conditions of use. Especially good results have been obtained when R is a methyl group.

The scavenger precursor compounds described above can be located in various positions in the photographic element, such as in a silver halide emulsion layer or in the dye image-providing material layer. In these latter two locations, the compound would scavenge a portion of the oxidized developing agent before it can react with the dye image-providing material and therefore act as a competer for oxidized developer. Such competers are useful in diffusion transfer systems when development takes place at higher than optimum temperatures. For example, at high temperatures, such as 32° to 35° C., there can be excessive development, which causes more oxidized developing agent to be generated and more dye to be released. This will cause a significant loss in speed and an increase in $D_{max}$ and $D_{min}$. The presence of a competer will help to alleviate the problem somewhat by scavenging a portion of the oxidized developing agent to reduce the amount of dye released. The compound, when used as a competer, can be employed in any amount which is effective for the intended purpose. Good results have usually been obtained when the compound is employed in a coverage of from about 5 to 500 mg/m².

In a preferred embodiment of our invention, the scavenger precursor compound is ballasted and is located in the photographic element as an interlayer between the various emulsion layers. In this embodiment, the scavenger precursor compound has the following formula:

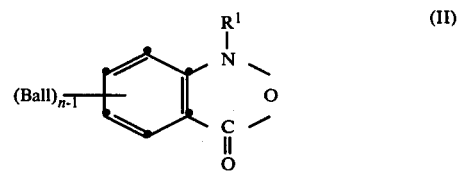

wherein:

R¹ is a substituted or unsubstituted alkyl or aryl group, as described above for R, or Ball;

Ball is at least one organic ballasting radical of such molecular size and configuration as to render the compound nondiffusible in the photographic element during development in an alkaline processing composition; and n is a positive integer of 1 to 3, with the proviso that when n is 1, then $R^1$ is Ball.

Such interlayers typically comprise the compound, gelatin, a coupler solvent, and other usual addenda. The compound can be employed in this embodiment in any amount which is effective for the intended purpose. Good results have usually been obtained when the compound is employed in a coverage of from about 200 to 2,000 mg/m$^2$.

The nature of the ballasting radical Ball in the above formula (II) is not critical so long as it confers nondiffusibility to the compound. Typical ballast groups include long-chain alkyl radicals linked directly or indirectly to the compound, as well as aromatic radicals of the benzene and naphthalene series indirectly attached or fused directly to the benzene ring, etc. Useful ballast groups generally have at least 8 carbon atoms, such as substituted or unsubstituted alkyl groups of 8 to 22 carbon atoms, a carbamoyl radical having 8 to 30 carbon atoms, such as —CONH(CH$_2$)$_4$—O—C$_6$H$_3$(C$_5$H$_{11}$)$_2$, —CON(C$_{12}$H$_{25}$)$_2$, etc, a keto radical having 8 to 30 carbon atoms, such as —CO—C$_{17}$H$_{35}$, —CO—C$_6$H$_4$(t—C$_{12}$H$_{25}$), etc. In a preferred embodiment of the invention, n is 3 so that the compound contains at least two ballasting radicals. Especially good results have been obtained when each Ball comprises an organic ballasting radical which is $$-\underset{\underset{CH_3}{|}}{CON}CH_2CH_2SO_2NHC_{18}H_{37}, \quad -\underset{\underset{CH_3}{|}}{CON}CH_2CH_2NHSO_2CH_3,$$

$$-\underset{\underset{CH_3}{|}}{CON}C_{18}H_{37}, \quad -\underset{\underset{C_8H_{17}}{|}}{CON}CH_2CH_2NHSO_2CH_3,$$

$$-COOCH_2CH_2NHSO_2CH_3,$$

—CO—N⟨N—CO—C$_6$H$_3$(SO$_2$NHC$_{12}$H$_{25}$)$_2$⟩ or $$-\underset{\underset{CH_3}{|}}{CON}CH_2CH_2SO_2NH(CH_2)_4O-C_6H_3(C_5H_{11}\text{-}t)_2$$

The ballasting radicals may also include electron-withdrawing or electron-donating groups to alter the reaction rates of the compounds, as desired.

Other substituents may be put on the compounds of formulas (I) or (II) to impart other desirable properties, such as solubility, stability, compatibility with other components, etc.

Typical compounds included within the scope of the above formula (II) include the following:

(1) Structure with CONCH$_2$CH$_2$NHSO$_2$CH$_3$ (CH$_3$), N—CH$_3$, and CH$_3$—N—CH$_2$CH$_2$SO$_2$NHC$_{18}$H$_{37}$ substituents on a benzene ring with two C=O groups.

(2) Structure with CONCH$_2$CH$_2$NHSO$_2$CH$_3$ (CH$_3$), N—CH$_3$, and CH$_3$NC$_{18}$H$_{37}$ substituents.

(3) Structure with CONCH$_2$CH$_2$NHSO$_2$CH$_3$ (CH$_3$), N—CH$_3$, and CH$_3$NCH$_2$CH$_2$NHSO$_2$CH$_3$ substituents.

(4) Structure with CONCH$_2$CH$_2$NHSO$_2$CH$_3$ (C$_8$H$_{17}$), N—CH$_3$, and CH$_3$NCH$_2$CH$_2$SO$_2$NHC$_{18}$H$_{37}$ substituents.

(5) Structure with CONCH$_2$CH$_2$SO$_2$NHC$_{18}$H$_{37}$ (CH$_3$), N—CH$_3$, and CH$_3$NCH$_2$CH$_2$SO$_2$NHC$_{18}$H$_{37}$ substituents.

(6) Structure with N(CH$_3$) group, piperazine linkage to phenyl bearing SO$_2$NHC$_{12}$H$_{25}$ groups.

(7) Structure with O=C—OCH$_2$CH$_2$NHSO$_2$CH$_3$, N—CH$_3$, and CH$_3$NCH$_2$CH$_2$SO$_2$NHC$_{18}$H$_{37}$ substituents.

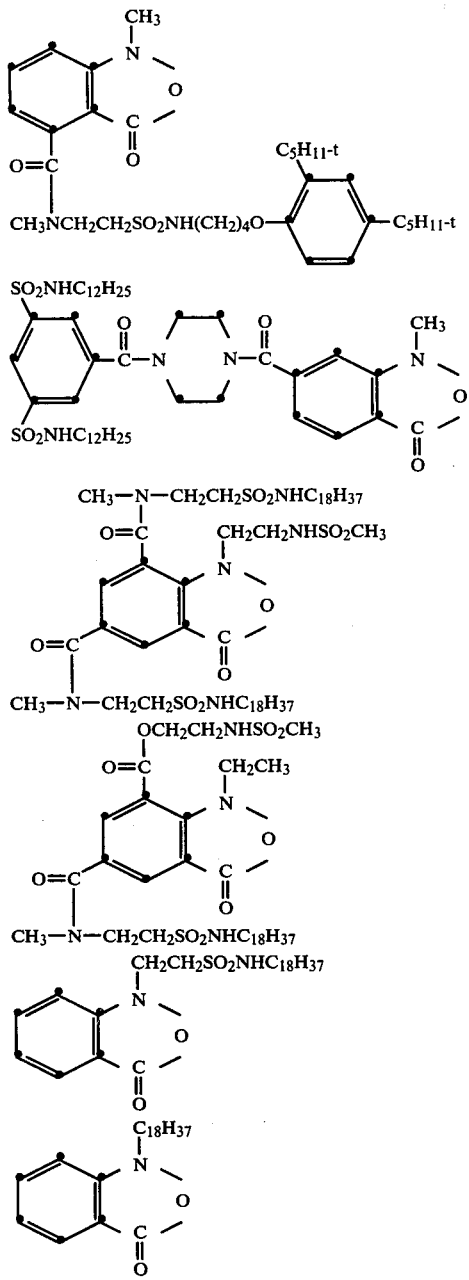

Compounds within the scope of the above formula (I) include the compounds listed above without the ballast groups on the benzene ring.

While it is not intended to limit the present invention to any particular theory or reaction mechanism, it is believed that the following chemical reactions take place in accordance with the process of the invention employing a preferred compound:

(1) Development of a latent silver halide image with ETA $$ETA + Ag^+ \rightarrow ETA_{ox} + Ag^\circ$$

(2) Ring opening of scavenger precursor compound in the presence of alkaline solution

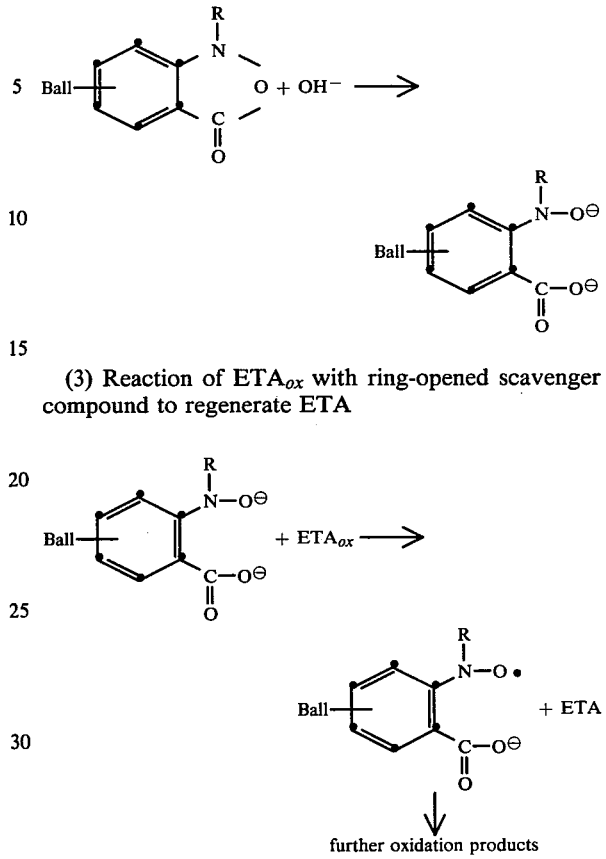

(3) Reaction of $ETA_{ox}$ with ring-opened scavenger compound to regenerate ETA As stated above, the dye image-providing materials useful in our invention are negative-working. Such materials include couplers which react with oxidized, aromatic, primary amino color developing agents to produce or release a dye. These conventional dye-forming couplers are well known to those skilled in the art and include, for example, two- and four-equivalent couplers of the open-chain ketomethylene, pyrazolone, pyrazolotriazole, pyrazolobenzimidazole, phenol and naphthol types. Other negative-working imaging chemistry utilizing the release of diffusible dyes from an immobile dye image-forming material as a function of development is illustrated, for example, by Whitmore et al, U.S. Pat. No. 3,227,550 and Canadian Pat. No. 602,607.

In a preferred embodiment of our invention, the dye image-providing material is a negative-working, ballasted, redox-dye-releasing (RDR) compound. Such compounds are well known to those skilled in the art and are, generally speaking, compounds which will redox with oxidized developing agent or ETA to release a dye, such as by alkaline hydrolysis. Such nondiffusible RDR's are described, for example, in U.S. Pat. Nos. 3,728,113 of Becker et al; 3,725,062 of Anderson and Lum; 3,698,897 of Gompf and Lum; 3,628,952 of Puschel et al; 3,443,939 and 3,443,940 of Bloom et al; 4,053,312 of Fleckenstein; 4,076,529 of Fleckenstein et al; 4,055,428 of Koyama et al; German Patents 2,505,248 and 2,729,820; Research Disclosure 15157, November, 1976; and Research Disclosure 15654, April, 1977. In a more preferred embodiment of our invention, the nondiffusible RDR's are ballasted p-sulfonamidonaphthol compounds, each of which has a color-providing moiety attached thereto through a sulfonamido group which is alkali-cleavable upon oxidation.

A process for producing a photographic image in color according to our invention comprises:

treating an imagewise-exposed photographic element, as described above, with an alkaline processing composition in the presence of a silver halide developing agent to effect development of each exposed silver halide emulsion layer, whereby:

(a) an imagewise distribution of dye is formed as a function of the development of the silver halide emulsion layer; and (b) at least a portion of the imagewise distribution of the dye diffuses out of the element, such as to a dye image-receiving layer.

A process for producing a photographic image in color according to our invention using a preferred element as described above wherein the nondiffusible RDR is a ballasted compound having a color-providing moiety attached thereto through a sulfonamido group which is alkali-cleavable upon oxidation comprises:

treating said element which has been imagewise-exposed with an alkaline processing composition in the presence of a silver halide developing agent to effect development of each exposed silver halide emulsion layer, whereby:

(a) the developing agent becomes oxidized;

(b) the oxidized developing agent cross-oxidizes the sulfonamido compound;

(c) the oxidized sulfonamido compound then cleaves, thus forming an imagewise distribution of the color-providing moiety as a function of the development of the silver halide emulsion layer; and (d) at least a portion of the imagewise distribution of the color-providing moiety diffuses out of the element, such as to a dye image-receiving layer.

It will be appreciated that, after processing the photographic elements described above, there remains in the elements, after transfer has taken place, an imagewise distribution of dye in addition to developed silver. A color image comprising residual nondiffusible compound may be obtained in these elements if the residual silver and silver halide are removed in any conventional manner well known to those skilled in the photographic art, such as a bleach bath followed by a fix bath, a bleach-fix bath, etc. The imagewise distribution of dye may also diffuse out of these elements into these baths, if desired, rather than to an image-receiving element.

The photographic element in the above-described processes can be treated with an alkaline processing composition to effect or initiate development in any manner. A preferred method for applying processing composition is by use of a rupturable container or pod which contains the composition. In general, the processing composition employed in this invention contains the developing agent for development, although the composition could also be solely an alkaline solution where the developer is incorporated in the photographic element, the image-receiving element or the process sheet, in which case the alkaline solution serves to activate the incorporated developer.

A photographic film unit or assemblage in accordance with this invention is adapted to be processed by an alkaline processing composition, and comprises:

(1) a photographic element as described above; and (2) a dye image-receiving layer.

In this embodiment, the processing composition may be inserted into the film unit, such as by interjecting processing solution with communicating members similar to hypodermic syringes which are attached either to a camera or camera cartridge. The processing composition may also be applied by means of a swab or by dipping in a bath, if so desired.

In a preferred embodiment of the invention, the assemblage itself contains the alkaline processing composition and means containing same for discharge within the film unit, such as a rupturable container which is adapted to be positioned during processing of the film unit so that a compressive force applied to the container by pressure-applying members, such as would be found in a camera designed for in-camera processing, will effect a discharge of the container's contents within the film unit.

The dye image-receiving layer in the above-described film unit can be located on a separate support adapted to be superposed on the photographic element after exposure thereof. Such image-receiving elements are generally disclosed, for example, in U.S. Pat. No. 3,362,819. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

The dye image-receiving layer in the above-described film unit can also be located integral with the photographic element between the support and the lowermost photosensitive silver halide emulsion layer. One useful format for integral receiver-negative photographic elements is disclosed in Belgian Pat. No. 757,960. In such an embodiment, the support for the photographic element is transparent and is coated with an image-receiving layer, a substantially opaque light-reflective layer, e.g., $TiO_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer, and dye images, formed as a function of development, diffuse to the image-receiving layer to provide a positive, right-reading image which is viewed through the transparent support on the opaque reflecting layer background. For other details concerning the format of this particular integral film unit, reference is made to the above-mentioned Belgian Pat. No. 757,960.

Another format for integral negative-receiver photographic elements in which the present invention can be employed is disclosed in Belgian Pat. No. 757,959. In this embodiment, the support for the photographic element is transparent and is coated with the image-receiving layer, a substantially opaque, light-reflective layer and the photosensitive layer or layers described above. A rupturable container, containing an alkaline processing composition and an opacifier, is positioned between the top layer and a transparent cover sheet which has thereon a neutralizing layer and a timing layer. The film unit is placed in a camera, exposed through the transparent cover sheet and then passed through a pair of pressure-applying members in the camera as it is being removed therefrom. The pressure-applying members rupture the container and spread processing composition and opacifier over the negative portion of the film unit to render it light-insensitive. The processing composition develops each silver halide layer and dye images, formed as a result of development, diffuse to the image-receiving layer to provide a positive, right-reading image which is viewed through the transparent support on the opaque reflecting layer background. For further details concerning the format of this particular integral film unit, reference is made to the above-mentioned Belgian Pat. No. 757,959.

Still other useful integral formats in which this invention can be employed are described in U.S. Pat. Nos. 3,415,644; 3,415,645; 3,415,646; 3,647,437; and 3,635,707. In most of these formats, a photosensitive silver halide emulsion is coated on an opaque support, and a dye image-receiving layer is located on a separate transparent support superposed over the layer outermost from the opaque support. In addition, this transparent support also preferably contains a neutralizing layer and a timing layer underneath the dye image-receiving layer.

Another embodiment of the invention uses the image-reversing technique disclosed in British Pat. No. 904,364, page 19, lines 1 through 41. In this process, the dye-releasing compounds are used in combination with physical development nuclei in a nuclei layer contiguous to the photosensitive silver halide negative emulsion layer. The film unit contains a silver halide solvent, preferably in a rupturable container with the alkaline processing composition.

The film unit or assembly of the present invention may be used to produce positive images in single- or multicolors. In a three-color system, each silver halide emulsion layer of the film assembly will have associated therewith a dye image-providing material which possesses a predominant spectral absorption within the region of the visible spectrum to which said silver halide emulsion is sensitive, i.e., the blue-sensitive silver halide emulsion layer will have a yellow dye image-providing material associated therewith, the green-sensitive silver halide emulsion layer will have a magenta dye image-providing material associated therewith, and the red-sensitive silver halide emulsion layer will have a cyan dye image-providing material associated therewith. The dye image-providing material associated with each silver halide emulsion layer may be contained either in the silver halide emulsion layer itself or in a layer contiguous to the silver halide emulsion layer, i.e., the dye image-providing material may be coated in a separate layer underneath the silver halide emulsion layer with respect to the exposure direction.

The concentration of the dye image-providing material that is employed in the present invention may be varied over a wide range, depending upon the particular compound employed and the results desired. For example, the dye image-providing material may be coated in a layer at a concentration of 0.1 to 3 g/m$^2$. The dye image-providing material may be dispersed in a hydrophilic film-forming natural material or synthetic polymer, such as gelatin, polyvinyl alcohol, etc, which is adapted to be permeated by aqueous alkaline processing composition.

A variety of silver halide developing agents can be employed in this invention. Specific examples of developers or ETA compounds which can be employed in this invention include hydroquinone compounds, such as hydroquinone, 2,5-dichlorohydroquinone, 2-chlorohydroquinone and the like; aminophenol compounds, such as 4-aminophenol, N-methylaminophenol, N,N-dimethylaminophenol, 3-methyl-4-aminophenol, 3,5-dibromoaminophenol and the like; catechol compounds, such as catechol, 4-cyclohexylcatechol, 3-methoxycatechol, 4-(N-octadecylamino)catechol and the like; phenylenediamine compounds, such as N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine and the like. In highly preferred embodiments, the ETA is a 3-pyrazolidinone compound, such as 1-phenyl-3-pyrazolidinone (Phenidone), 1-phenyl-4,4-dimethyl-3-pyrazolidinone (Dimezone), 4-hydroxymethyl-4-methyl-1-phenyl-3-pyrazolidinone, 4-hydroxymethyl-4-methyl-1-p-tolyl-3-pyrazolidinone, 4-hydroxymethyl-4-methyl-1-(3,4-dimethylphenyl)-3-pyrazolidinone, 1-m-tolyl-3-pyrazolidinone, 1-p-tolyl-3-pyrazolidinone, 1-phenyl-4-methyl-3-pyrazolidinone, 1-phenyl-5-methyl-3-pyrazolidinone, 1-phenyl-4,4-dihydroxymethyl-3-pyrazolidinone, 1,4-dimethyl-3-pyrazolidinone, 4-methyl-3-pyrazolidinone, 4,4-dimethyl-3-pyrazolidinone, 1-(3-chlorophenyl)-4-methyl-3-pyrazolidinone, 1-(4-chlorophenyl)-4-methyl-3-pyrazolidinone, 1-(3-chlorophenyl)-3-pyrazolidinone, 1-(4-chlorophenyl)-3-pyrazolidinone, 1-(4-tolyl)-4-methyl-3-pyrazolidinone, 1-(2-tolyl)-4-methyl-3-pyrazolidinone, 1-(4-tolyl)-3-pyrazolidinone, 1-(3-tolyl)-3-pyrazolidinone, 1-(3-tolyl)-4,4-dimethyl-3-pyrazolidinone, 1-(2-trifluoroethyl)-4,4-dimethyl-3-pyrazolidinone, 5-methyl-3-pyrazolidinone, and the like. A combination of different ETA's, such as those disclosed in U.S. Pat. No. 3,039,869, can also be employed. Such developing agents can be employed in the liquid processing composition or may be contained, at least in part, in any layer or layers of the photographic element or film unit to be activated by the alkaline processing composition, such as in the silver halide emulsion layers, the dye image-providing material layers, interlayers, image-receiving layer, etc.

In using dye image-providing materials in the invention which produce diffusible dye images as a function of development, either conventional negative-working or direct-positive silver halide emulsions may be employed. If the silver halide emulsion employed is a direct-positive silver halide emulsion, such as an internal-image emulsion designed for use in the internal image reversal process, or a fogged, direct-positive emulsion such as a solarizing emulsion, which is developable in unexposed areas, a positive image can be obtained on the dye image-receiving layer by using ballasted, redox, dye-releasers. After exposure of the film unit, the alkaline processing composition permeates the various layers to initiate development of the exposed photosensitive silver halide emulsion layers. The developing agent present in the film unit develops each of the silver halide emulsion layers in the unexposed areas (since the silver halide emulsions are direct-positive ones), thus causing the developing agent to become oxidized imagewise corresponding to the unexposed areas of the direct-positive silver halide emulsion layers. The oxidized developing aget then cross-oxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a pH-lowering layer in the film unit or image-receiving unit lowers the pH of the film unit or image receiver to stabilize the image.

Internal-image silver halide emulsions useful in this invention are described more fully in the November 1976 edition of *Research Disclosure*, pages 76 through 79, the disclosure of which is hereby incorporated by reference.

The various silver halide emulsion layers of a color film assembly employed in this invention can be disposed in the usual order, i.e., the blue-sensitive silver halide emulsion layer first with respect to the exposure side, followed by the green-sensitive and red-sensitive silver halide emulsion layers. If desired, a yellow dye layer or a yellow colloidal silver layer can be present between the blue-sensitive and green-sensitive silver halide emulsion layers for absorbing or filtering blue radiation that may be transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention can be of the type disclosed in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed in gelatin and are about 0.6 to 6 microns in thickness; the dye image-providing materials are dispersed in an aqueous alkaline solution-permeable polymeric binder, such as gelatin, as a separate layer about 0.2 to 7 microns in thickness; and the alkaline solution-permeable polymeric interlayers, e.g., gelatin, are about 0.2 to 5 microns in thickness. Of course, these thicknesses are approximate only and can be modified according to the product desired.

Any material can be employed as the image-receiving layer in this invention as long as the desired function of mordanting or otherwise fixing the dye images is obtained. The particular material chosen will, of course, depend upon the dye to be mordanted. Suitable materials are disclosed on pages 80 through 82 of the November 1976 edition of *Research Disclosure*, the disclosure of which is hereby incorporated by reference.

Use of a pH-lowering material in the film units of this invention will usually increase the stability of the transferred image. Generally, the pH-lowering material will effect a reduction in the pH of the image layer from about 13 or 14 to at least 11 and preferably 5 to 8 within a short time after imbibition. Suitable materials and their functions are disclosed on pages 22 and 23 of the July, 1974 edition of *Research Disclosure*, and on pages 35 through 37 of the July 1975 edition of *Research Disclosure*, the disclosures of which are hereby incorporated by reference.

A timing or inert spacer layer can be employed in the practice of this invention over the pH-lowering layer which "times" or controls the pH reduction as a function of the rate at which the alkaline composition diffuses through the inert spacer layer. Examples of such timing layers and their functions are disclosed in the *Research Disclosure* articles mentioned in the paragraph above concerning pH-lowering layers.

The alkaline processing composition employed in this invention is the conventional aqueous solution of an alkaline material, e.g., alkali metal hydroxides or carbonates such as sodium hydroxide, sodium carbonate or an amine such as diethylamine, preferably possessing a pH in excess of 11, and preferably containing a developing agent as described previously. Suitable materials and addenda frequently added to such compositions are disclosed on pages 79 and 80 of the November 1976 edition of *Research Disclosure*, the disclosure of which is hereby incorporated by reference.

The alkaline solution-permeable, substantially opaque, light-reflective layer employed in certain embodiments of photographic film units used in this invention are described more fully in the November 1976 edition of *Research Disclosure*, page 82, the disclosure of which is hereby incorporated by reference.

The supports for the photographic elements used in this invention can be any material, as long as it does not deleteriously affect the photographic properties of the film unit and is dimensionally stable. Typical flexible sheet materials are described on page 85 of the November 1976 edition of *Research Disclosure*, the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone.

The silver halide emulsions useful in this invention, both negative-working and direct-positive ones, are well known to those skilled in the art and are described in *Product Licensing Index*, Volume 92, December 1971, publication 9232, page 107, paragraph I, "Emulsion types"; they may be chemically and spectrally sensitized as described on page 107, paragraph III, "Chemical sensitization", and pages 108 and 109, paragraph XV, "Spectral sensitization", of the above article; they can be protected against the production of fog and can be stabilized against loss of sensitivity during keeping by employing the materials described on page 107, paragraph V, "Antifoggants and stabilizers", of the above article; they can contain development modifiers, hardeners, and coating aids as described on pages 107 and 108, paragraph IV, "Development modifiers"; paragraph VII, "Hardeners"; and paragraph XII, "Coating aids", of the above article; they and other layers in the photographic elements used in this invention can contain plasticizers, vehicles and filter dyes described on page 108, paragraph XI, "Plasticizers and lubricants", and paragraph VIII, "Vehicles", and page 109, paragraph XVI, "Absorbing and filter dyes", of the above article; they and other layers in the photographic elements used in this invention may contain addenda which are incorporated by using the procedures described on page 109, paragraph XVII, "Methods of addition", of the above article; and they can be coated by using the various techniques described on page 109, paragraph XVIII, "Coating procedures", of the above article, the disclosures of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium. "Mobile" has the same meaning as "diffusible".

The term "associated therewith" as used herein is intended to mean that the materials can be in either the same or different layers so long as the materials are accessible to one another.

The following example is provided to further illustrate the invention.

EXAMPLE—Preparation and Photographic Testing of Integral Imaging Receiving Element To evaluate compounds with respect to their effectiveness as interlayer scavengers for oxidized developing agent, the following two-color image transfer elements were prepared by coating the following layers in the order recited on a transparent poly(ethylene terephthalate) film support. Quantities are parenthetically given in g/m², unless otherwise stated.

(1) image-receiving layer of a poly(divinylbenzene-co-styrene-co-N-benzyl-N,N-dimethyl-N-vinylbenzyl-)ammonium chloride latex mordant (2.29) and gelatin (2.29);

(2) reflecting layer of titanium dioxide (16.2) and gelatin (2.59);

(3) opaque layer of carbon black (1.89) and gelatin (1.24);

(4) cyan dye-providing layer of gelatin (1.22), cyan RDR Compound A (0.54), and 1,4-cyclohexylenedimethylenebis(2-ethylhexanoate) (0.27);

(5) red-sensitive, direct-positive silver bromide emulsion (silver - 1.30, gelatin 1.35), 2-(2-octadecyl-5-sulfohydroquinone potassium salt (0.17), 1-[4-(2-formylhydrazino)phenyl]-3-phenylthiourea (3.84 mg/mole of silver), and aceto-2-{p-[5-amino-2-(2,4-di-t-pentylphenoxy)benzamido]phenyl}hydrazide (328 mg/mole of silver);

(6) interlayer of gelatin (2.16) and scavenger compounds* 1, 2, 3, 4, 5, 6, 7, 8 and 9, as shown above, and Prior Art Scavenger A, in the amounts shown in the Table; and (7) yellow dye-providing layer of gelatin (1.46), yellow RDR Compound B (0.64); and 1,4-cyclohexylenedimethylene-bis(2-ethylhexanoate) (0.32).

\* Each scavenger was dissolved in one-half its weight of 1,4-cyclohexylenedimethylene-bis(2-ethylhexanoate) and dispersed in the gelatin before coating.

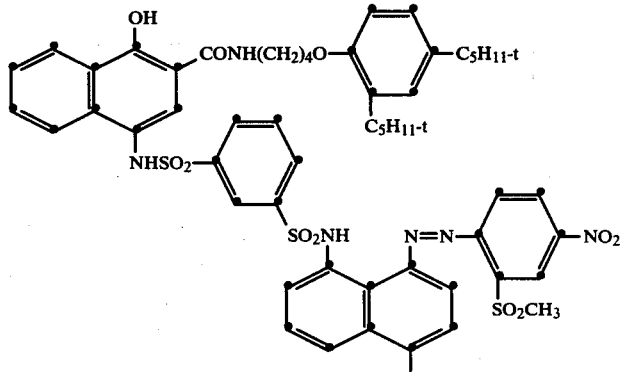

CYAN RDR COMPOUND A

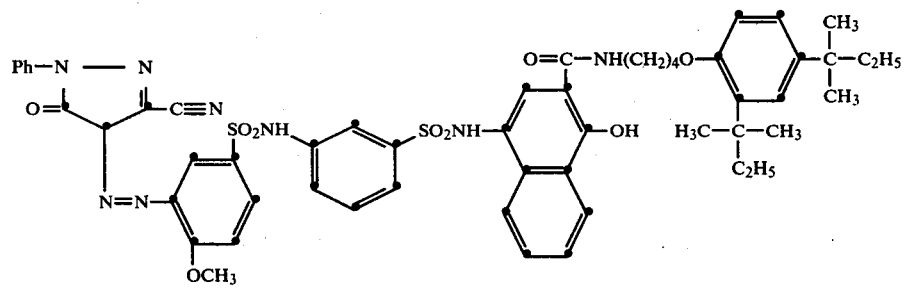

YELLOW RDR COMPOUND B

PRIOR ART SCAVENGER A

-continued

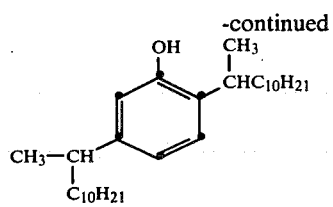

One sample of each of the above-prepared photosensitive elements was exposed through a graduated-density test object. The exposed samples were then processed at 70° F. (21° C.) by rupturing a pod containing a viscous processing composition between the photosensitive element and a transparent cover sheet, as described below.

The processing composition was as follows:

| | |
|---|---|
| Potassium hydroxide | 65.0 g |
| Sodium sulfite | 1.0 g |
| 5-Methylbenzotriazole | 3.8 g |
| 4-Hydroxymethyl-4-methyl-1-phenyl-3-pyrazolidone | 12.0 g |
| Potassium fluoride | 10.0 g |
| t-Butylhydroquinone | 0.3 g |
| Methylhydroquinone | 0.1 g |
| Carbon dispersion | 172.0 g Carbon |
| Carboxymethyl cellulose | 44.0 g |
| Water to 1.0 liter | |

The cover sheet consisted of a transparent poly(ethylene terephthalate) film support having coated thereon:
(1) a polyacrylic acid layer (188 meq/m$^2$)
(2) a timing layer comprising 2.16 g/m$^2$ of a mixture of 89 percent cellulose acetate (40 percent acetyl) and 11 percent poly(styrene-co-maleic anhydride) (approximately 50 percent hydrolyzed)
(3) a second timing layer comprising 2.16 g/m$^2$ of a latex dispersion of poly(acrylonitrile-co-vinylidene chloride-co-acrylic acid)

Additional samples of each photosensitive element were incubated for two weeks and four weeks at 120° F. (48.8° C.) and 50 percent relative humidity in a pure oxygen atmosphere. This served as an accelerated test to represent room temperature keeping for about six months and about one year, respectively. After incubating, the samples were exposed and processed as described above.

The effectiveness of compounds 1, 2, 3, 4, 5, 6, 7, 8 and 9 as interlayer scavengers for oxidized ETA relative to a prior art scavenger was determined by measuring the amount of yellow dye contamination (blue density) in the final cyan (red density) image, before and after incubation. An effective scavenger for oxidized ETA must be sufficiently reactive to prevent color contamination, yet not be so reactive as to result in significant loss to the image dye density.

The results for each of the tested compounds are shown in the following table, wherein the red $D_{max}$ indicates the maximum amount of cyan image dye transferred to the receiving layer, and the values stated for blue $D_{max}$ have been corrected to exclude the unwanted blue absorption of the cyan dye so as to represent the amount of yellow dye contamination caused by the yellow RDR in the indicating layer of the model elements.

TABLE

| Element with Scavenger Compound | Quantity (mg/m$^2$) | Red $D_{max}$ | | | Blue $D_{max}$ (Yellow Contamination) | | |
|---|---|---|---|---|---|---|---|
| | | Fresh | Two Weeks | Four Weeks | Fresh | Two Weeks | Four Weeks |
| None | (Gel interlayer control) | 1.75 | 1.89 | 1.92 | 0.80 | 0.84 | 0.88 |
| A (control) | 710 | 1.41 | 1.88 | 2.12 | 0.04 | 0.45 | 0.78 |
| 1 | 1183 | 1.10 | 1.55 | 1.64 | 0.01 | 0.02 | 0.03 |
| 2 | 1011 | 1.52 | 1.87 | 1.96 | 0.22 | 0.24 | 0.28 |
| 3 | 807 | 1.21 | 1.57 | 1.65 | 0.23 | 0.42 | 0.48 |
| 4 | 1334 | 1.41 | 1.73 | 1.82 | 0.03 | 0.04 | 0.04 |
| 5 | 1549 | 1.58 | 1.97 | 1.96 | 0.10 | 0.29 | 0.27 |
| 6 | 1356 | 1.28 | 1.75 | 1.86 | 0.04 | 0.04 | 0.06 |
| 7 | 1162 | 1.26 | 2.00 | 2.05 | 0.15 | 0.59 | 0.72 |
| 8 | 958 | 1.38 | 1.88 | 1.94 | 0.04 | 0.13 | 0.21 |
| 9 | 689 | 1.25 | 1.80 | — | 0.07 | 0.06 | — |

In the control element which has no interlayer scavenger, the oxidized developing agent (4-hydroxymethyl-4-methyl-1-phenyl-3-pyrazolidone) migrated to the yellow RDR layer, reacted with the RDR to release a diffusible yellow dye, which then caused the relative high blue density values. While the control element with prior art scavenger A was effective in scavenging oxidized ETA in the fresh sample, it was not as effective in the four-week incubation test. When the compounds of the invention were used as scavengers, however, the blue densities were significantly reduced, thus indicating that they were highly effective in scavenging the oxidized developing agent, both in the fresh samples and after incubation.

The invention has been described in detail with particular reference to preferred embodiments thereof, but it will be understood that variations and modifications can be effected within the spirit and scope of the invention.

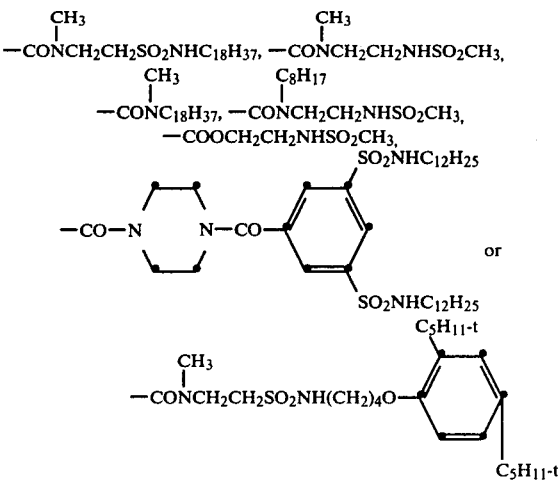

What is claimed is:
1. In a photographic element comprising a support having thereon at least one photosensitive silver halide emulsion layer having associated therewith a negative-working, dye image-providing material which produces an imagewise distribution of diffusible dye in the areas where said silver halide is developed, the improvement wherein said element contains an N-alkyl- or N-aryl-benzisoxazolone compound.

2. The photographic element of claim 1 wherein said compound has the following formula:

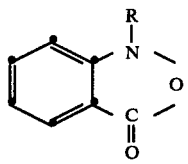

wherein:
R represents a substituted or unsubstituted alkyl or aryl group.

3. The photographic element of claim 2 wherein said compound is located in said silver halide emulsion layer.

4. The photographic element of claim 2 wherein said compound is located in a layer with said dye image-providing material.

5. The photographic element of claim 2 wherein said dye image-providing material is a ballasted, redox-dye-releasing compound.

6. The photographic element of claim 5 wherein said dye-releasing compound is a p-sulfonamidonaphthol.

7. The photographic element of claim 2 wherein R is a methyl group.

8. In a photographic element comprising a support having thereon at least two photosensitive silver halide emulsion layers, each emulsion layer having associated therewith a negative-working, dye image-providing material, the improvement wherein said element also contains in an interlayer between said emulsion layers having the following formula:

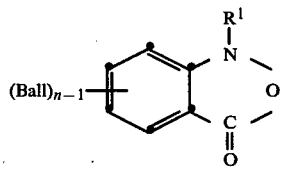

wherein:
R$^1$ represents a substituted or unsubstituted alkyl or aryl group, or Ball;
Ball is at least one organic ballasting radical of such molecular size and configuration as to render said compound nondiffusible in said photographic element during development in an alkaline processing composition; and
n is a positive integer of 1 to 3, with the proviso that when n is 1, then R$^1$ is Ball, said compound being separate and distinct from said dye image-providing material.

9. The photographic element of claim 8 wherein each said Ball is

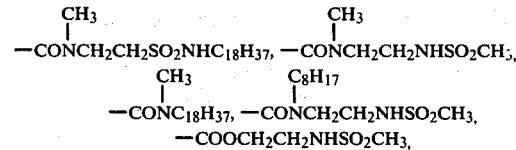

10. In a photographic element comprising a support having thereon a red-sensitive silver halide emulsion layer having a negative-working, cyan dye image-providing material associated therewith, an interlayer, a green-sensitive silver halide emulsion layer having a negative-working, magenta dye image-providing material associated therewith, an interlayer, and a blue-sensitive silver halide emulsion layer having a negative-working, yellow dye image-providing material associated therewith, the improvement wherein each said interlayer comprises a compound having the following formula:

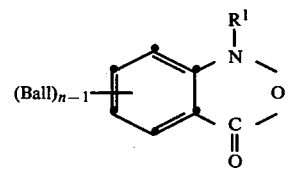

wherein:
R$^1$ represents a substituted or unsubstituted alkyl or aryl group, or Ball;
Ball is at least one organic ballasting radical of such molecular size and configuration as to render said compound nondiffusible in said photographic element during development in an alkaline processing composition; and
n is a positve integer of 1 to 3, with the pro·iso that when n is 1, then R$^1$ is Ball, said compound being separate and distinct from said dye image-providing materials.

11. The photographic element of claim 10 wherein said dye image-providing material is a ballasted, redox-dye-releasing compound.

12. The photographic element of claim 11 wherein said dye-releasing compound is a p-sulfonamidonaphthol.

13. The photographic element of claim 10 wherein R$^1$ is a methyl group.

14. The photographic element of claim 13 wherein each said Ball is

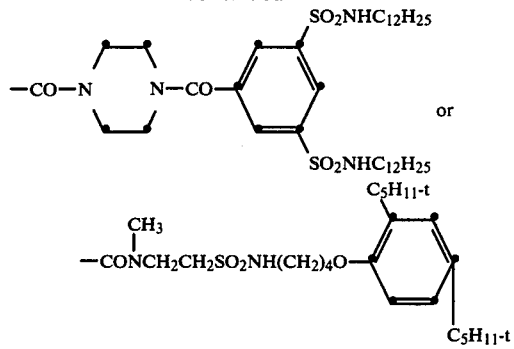

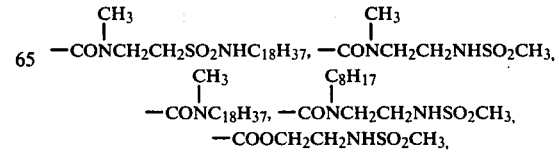

-continued

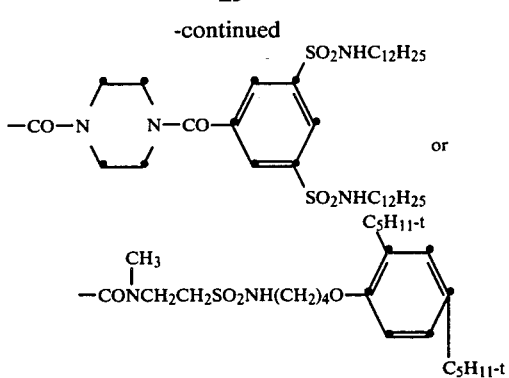
or

15. In a photographic assemblage to be processed by an alkaline processing composition, said assemblage comprising:
   (a) a photographic element comprising a support having thereon at least one photosensitive silver halide emulsion layer having associated therewith a negative-working, dye image-providing material which produces an imagewise distribution of diffusible dye in the areas where said silver halide is developed; and
   (b) a dye image-receiving layer;
the improvement wherein said photographic assemblage contains an N-alkyl- or N-aryl-benzisoxazolone compound.

16. In a photographic assemblage comprising:
   (a) a photographic element comprising a support having thereon at least one photosensitive silver halide emulsion layer having associated therewith a negative-working, dye image-providing material which produces an imagewise distribution of diffusible dye in the areas where said silver halide is developed;
   (b) a dye image-receiving layer; and
   (c) an alkaline processing composition and means containing same for discharge within said assemblage;
said assemblage containing a silver halide developing agent; the improvement wherein said photographic assemblage contains an N-alkyl- or N-aryl-benzisoxazolone compound.

17. The photographic assemblage of claim 16 wherein said compound has the following formula:

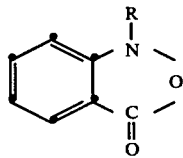

wherein:
   R represents a substituted or unsubstituted alkyl or aryl group.

18. The photographic assemblage of claim 17 wherein said compound is located in said silver halide emulsion layer.

19. The photographic assemblage of claim 17 wherein said compound is located in a layer with said dye image-providing material.

20. The photographic assemblage of claim 17 wherein said dye image-providing material is a ballasted, redox-dye-releasing compound.

21. The photographic assemblage of claim 20 wherein said dye-releasing compound is a p-sulfonamido-naphthol.

22. The photographic assemblage of claim 17 wherein R is methyl.

23. In a photographic assemblage comprising:
   (a) a photographic element comprising a support having thereon at least two photosensitive silver halide emulsion layers, each emulsion layer having associated therewith a negative-working, dye image-providing material;
   (b) a dye image-receiving layer; and
   (c) an alkaline processing composition and means containing same for discharge within said assemblage;
said assemblage containing a silver halide developing agent; the improvement wherein said element also contains in an interlayer between said emulsion layers a compound having the following formula:

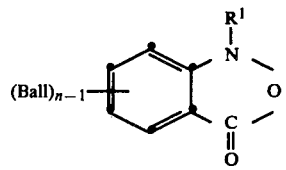

wherein:
   $R^1$ represents a substituted or unsubstituted alkyl or aryl group, or Ball;
   Ball is at least one organic ballasting radical of such molecular size and configuration as to render said compound nondiffusible in said photographic element during development in an alkaline processing composition; and
   n is a positive integer of 1 to 3, with the proviso that when n is 1, then $R^1$ is Ball, said compound being separate and distinct from said dye image-providing material.

24. The photographic assemblage of claim 23 wherein each said Ball is

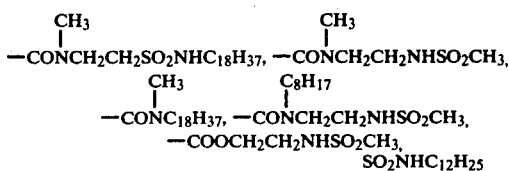

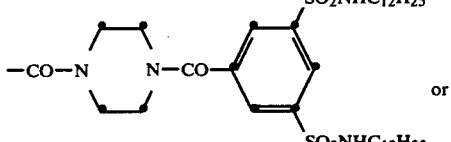

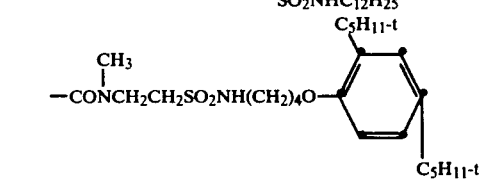

25. The photographic assemblage of claim 23 wherein:
   (a) said dye image-receiving layer is located between said support and said silver halide emulsion layers; and (b) said assemblage also includes a transparent cover sheet over the layer outermost from said support.

26. The photographic assemblage of claim 25 wherein said cover sheet has thereon, in sequence, a neutralizing layer and a timing layer.

27. The photographic assemblage of claim 26 wherein said discharging means is a rupturable container containing said alkaline processing composition and an opacifying agent, said container being so positioned during processing of said assemblage that a compressive force applied to said container will effect a discharge of the container's contents between said transparent sheet and the layer outermost from said support.

28. The photographic assemblage of claim 23 wherein said support having thereon said photosensitive silver halide emulsion layers is opaque and said dye image-receiving layer is located on a separate transparent support superposed over the layer outermost from said opaque support.

29. The photographic assemblage of claim 28 wherein said transparent support has thereon, in sequence, a neutralizing layer, a timing layer and said dye image-receiving layer.

30. In a photographic assemblage comprising:
(a) a photographic element comprising a support having thereon a red-sensitive silver halide emulsion layer having associated therewith a negative-working, cyan dye image-providing material, an interlayer, a green-sensitive silver halide emulsion layer having associated therewith a negative-working, magenta dye image-providing material, an interlayer, and a blue-sensitive silver halide emulsion layer having associated therewith a negative-working, yellow dye image-providing material;
(b) a dye image-receiving layer; and
(c) an alkaline processing composition and means containing same for discharge within said assemblage;

said assemblage containing a silver halide developing agent; the improvement wherein each said interlayer comprises a compound having the formula:

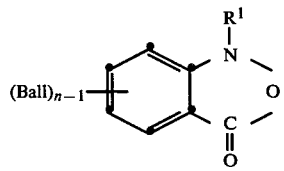

wherein:
R¹ represents a substituted or unsubstituted alkyl or aryl group, or Ball;
Ball is at least one organic ballasting radical of such molecular size and configuration as to render said compound nondiffusible in said photographic element during development in an alkaline processing composition; and
n is a positive integer of 1 to 3, with the proviso that when n is 1, then R¹ is Ball, said compound being separate and distinct from said dye image-providing materials.

31. In an integral photographic assemblage comprising:
(a) a photosensitive element comprising a transparent support having thereon the following layers in sequence: a dye image-receiving layer, an alkaline solution-permeable, light-reflective layer, an alkaline solution-permeable, opaque layer, a red-sensitive silver halide emulsion layer having associated therewith a negative-working, cyan dye image-providing material, an interlayer, a green-sensitive silver halide emulsion layer having associated therewith a negative-working, magenta dye image-providing material, an interlayer, and a blue-sensitive silver halide emulsion layer having associated therewith a negative-working, yellow dye image-providing material;
(b) a transparent sheet superposed over said blue-sensitive silver halide emulsion layer and comprising a transparent support having thereon, in sequence, a neutralizing layer and a timing layer; and
(c) a rupturable container containing an alkaline processing composition and an opacifying agent which is so positioned during processing of said assemblage that a compressive force applied to said container will effect a discharge of the container's contents between said transparent sheet and said blue-sensitive silver halide emulsion layer;

said assemblage containing a silver halide developing agent; the improvement wherein each said interlayer comprises a compound having the formula:

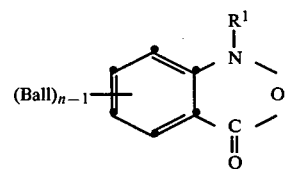

wherein:
R¹ represents a substituted or unsubstituted alkyl or aryl group, or Ball;
Ball is at least one organic ballasting radical of such molecular size and configuration as to render said compound nondiffusible in said photographic element during development in an alkaline processing compositon; and
n is a positive integer of 1 to 3, with the proviso that when n is 1, then R¹ is Ball, said compound being separate and distinct from said dye image-providing materials.

32. In a process for producing a photographic image in color in an imagewise-exposed photographic element comprising a support having thereon at least one photosensitive silver halide emulsion layer having associated therewith a negative-working, dye image-providing material which produces an imagewise distribution of diffusible dye in the areas where said silver halide is developed, said process comprising:
treating said element with an alkaline processing composition in the presence of a silver halide developing agent to effect development of each exposed silver halide emulsion layer, whereby:
(a) an imagewise distribution of said dye is formed as a function of said development of said silver halide emulsion layer; and
(b) at least a portion of said imagewise distribution of said dye diffuses out of said element,
the improvement wherein said process is performed in the presence of an N-alkyl- or N-aryl-benzisoxazolone compound.

33. The process of claim 32 wherein said compound has the following formula:

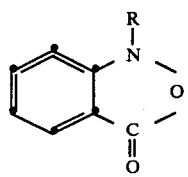

wherein:
R represents a substituted or unsubstituted alkyl or aryl group.

34. The process of claim 33 wherein said imagewise distribution of said dye diffuses to a dye image-receiving layer.

35. The process of claim 33 wherein said compound is located in said silver halide emulsion layer.

36. The process of claim 33 wherein said compound is located in a layer with said dye image-providing material.

37. The process of claim 33 wherein said dye image-providing material is a ballasted, redox-dye-releasing compound.

38. The process of claim 37 wherein said dye-releasing compound is a p-sulfonamidonaphthol.

39. The process of claim 33 wherein R is a methyl group.

40. The process of claim 33 wherein said photographic element comprises a support having thereon a red-sensitive silver halide emulsion layer having a negative-working, cyan dye image-providing material associated therewith, an interlayer, a green-sensitive silver halide emulsion layer having a negative-working, magenta dye image-providing material associated therewith, an interlayer, and a blue-sensitive silver halide emulsion layer having a negative-working, yellow dye image-providing material associated therewith, and said compound is located in each said interlayer.

41. In a process for producing a photographic image in color in an imagewise-exposed photographic element comprising a support having thereon at least two photosensitive silver halide emulsion layers, each emulsion layer having associated therewith a negative-working, dye image-providing material, said process comprising:
treating said element with an alkaline processing composition in the presence of a silver halide developing agent to effect development of each exposed silver halide emulsion layer, whereby:
(a) an imagewise distribution of said dye is formed as a function of said development of said silver halide emulsion layer; and
(b) at least a portion of said imagewise distribution of said dye diffuses out of said element,
the improvement wherein said process is performed in the presence of an N-alkyl- or N-aryl-benzisoxazolone compound which is located in said element in an interlayer between said emulsion layers, said compound having the following formula:

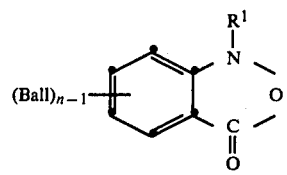

wherein:
$R^1$ represents a substituted or unsubstituted alkyl or aryl group, or Ball;
Ball is at least one organic ballasting radical of such molecular size and configuration as to render said compound nondiffusible in said photographic element during development in an alkaline processing composition; and
n is a positive integer of 1 to 3, with the proviso that when n is 1, then $R^1$ is Ball, said compound being separate and distinct from said dye image-providing material.

42. The process of claim 41 wherein each said Ball is